United States Patent [19]

Fischer et al.

[11] 4,089,768

[45] May 16, 1978

[54] BATTERY OPERATED WATER PURIFICATION SYSTEM

[75] Inventors: Wolfgang Fischer, Konigsberg; Bernd Hengst, Schweinfurt am Main, both of Germany

[73] Assignee: Sachs-Systemtechnik GmbH, Schweinfurt am Main, Germany

[21] Appl. No.: 804,561

[22] Filed: Jun. 8, 1977

[30] Foreign Application Priority Data

Jun. 14, 1976  Germany .............................. 2626569

[51] Int. Cl.² .................. C25B 15/02; C02B 1/82; C25C 3/20
[52] U.S. Cl. ..................... 204/228; 204/149; 204/237; 204/271
[58] Field of Search ............... 204/149, 228, 271, 237; 210/243

[56] References Cited

U.S. PATENT DOCUMENTS

| | | | |
|---|---|---|---|
| 3,544,442 | 12/1970 | Anderson | 204/271 X |
| 3,965,008 | 6/1976 | Dawson | 210/243 X |
| 4,006,071 | 2/1977 | Martchenke | 204/228 |
| 4,026,784 | 5/1977 | Rivers | 204/237 X |
| 4,054,503 | 10/1977 | Higgins | 204/271 |

Primary Examiner—Howard S. Williams
Assistant Examiner—D. R. Valentine

[57] ABSTRACT

An electrolytic water purification system operated from a battery includes an electrolytic cell which may purify water properly only when an applied voltage exceeds the battery output voltage. A power supply circuit energized by the battery furnishes the necessary higher voltage. An electrically driven pump is directly energized by the battery for pumping the water to be purified through the cell. The pump is automatically deenergized when the conductivity of the water or the available voltage is outside prescribed limits.

12 Claims, 4 Drawing Figures

BATTERY OPERATED WATER PURIFICATION SYSTEM

This invention relates to the electrolytic purification of water, and particularly to a water purification system operable by means of a dry cell battery or storage battery.

The known devices which purify water by anodic oxidation of contaminants, particularly microorganisms, are suitable mainly for stationary or otherwise permanent use. Yet, proper drinking water is usually more difficult to obtain in places only temporarily occupied or inhabitated, such as camp sites and weekend houses. Travelers not wishing to rely entirely on local water supply systems in foreign lands also may be in need of a self-contained and portable water purification system not available heretofore.

It is a primary object of this invention to provide an electrolytic water supply system which is self-contained and portable, sufficiently flexible to operate on a wide variety of water sources, and simple to operate, yet capable of reliably disinfecting water carrying pathogenic microorganisms.

The proper operation of an electrolytic cell for water purification requires an adequate current to be passed between electrodes of the cell and an adequate dwell time of the water in the cell. The current flow through the cell, under otherwise constant conditions, depends on the conductivity of the raw water which is not predictable and not capable of being controlled. With water low in mineral content, the conductivity may be quite low and is not affected by organic contaminants. A water purification system of the desired type thus should be capable of supplying a relatively high voltage. A portable, self-contained purification must be operated from batteries, and the weight of a battery, under otherwise constant conditions, is directly proportional to the output voltage. Yet, a portable water purification unit should be as light as possible.

To achieve its objects, the invention provides a water purification system including an electrolytic cell in which the dwell time of the water in the cell is maintained by a pump which supplies raw water to the cell and causes purified water to be discharged at a fixed rate. The pump is driven by an electric motor directly energized by the battery. The unit may employ a battery of relatively low output voltage and correspondingly low weight because a D.C. power supply circuit receiving energy from the battery furnishes a D.C. output voltage exceeding the battery voltage to the electrolytic cell.

To facilitate operation by unskilled personnel, automatic controls prevent operation of the unit and/or provide a sensible signal if conditions are not proper for producing water fit to be drunk.

Other features, additional objects, and many of the advantages of this invention will readily be appreciated as the same becomes better understood by reference to the following detailed description of a preferred embodiment when considered in connection with the appended drawing in which.

Figure 1:
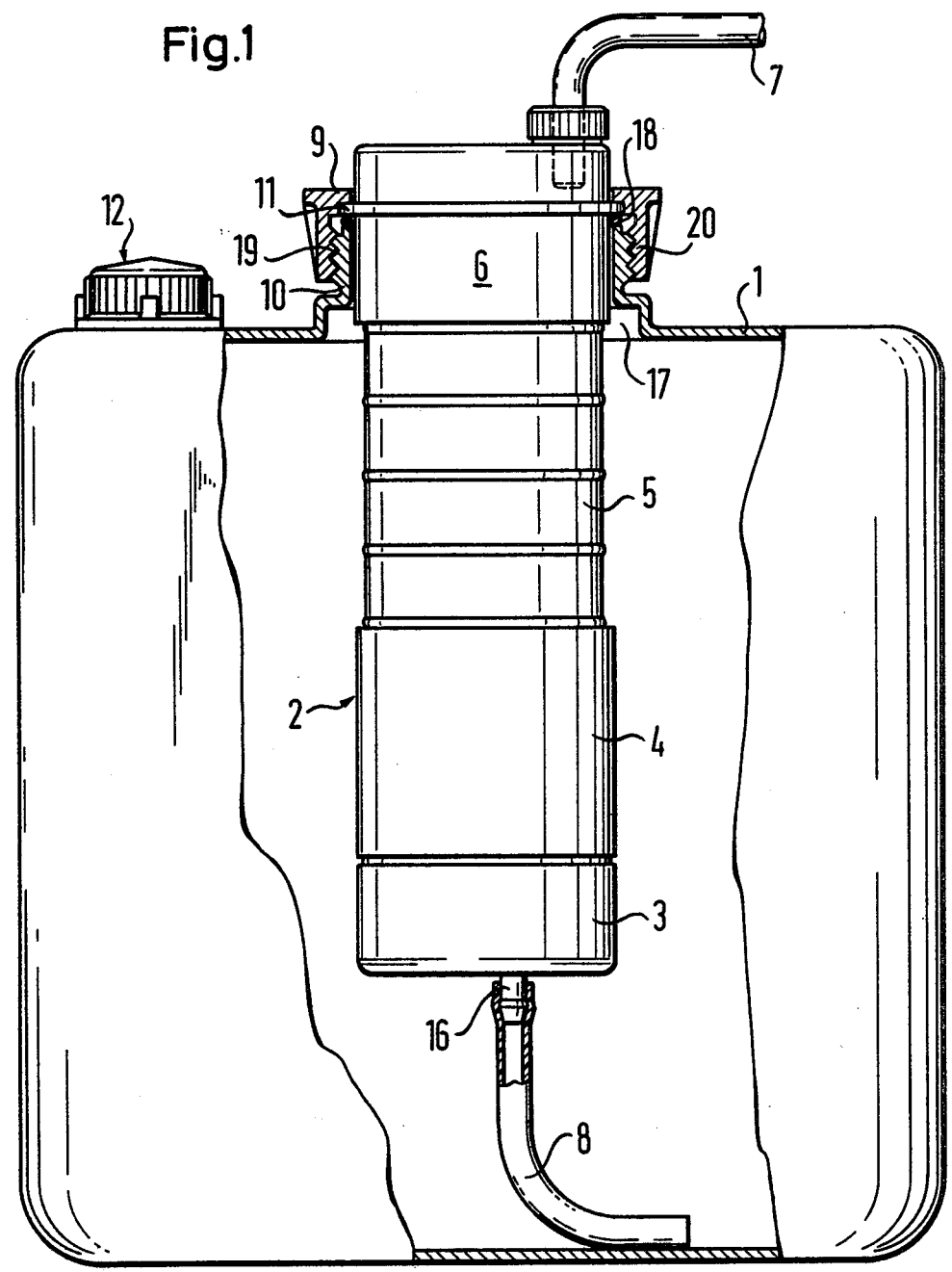
FIG. 1 shows a water purification system of the invention including a storage can with built-in purification unit in side elevation, the can being partly broken away to show its contents.

Referring initially to FIG. 1, there is seen a 5-gallon water storage can 1 of generally rectangular configuration whose top wall is provided with a normally capped filling nipple 12 and a much larger central nipple 10 extending upward from a circular aperture 17 in the can 1. The housing 2 of a purification unit is of generally circular cross section about a vertical axis and passes through the aperture 17. The topmost section 6 of the housing encloses a power supply and controls, as will presently be described with reference to FIGS. 3 and 4.

A radial flange 11 on the housing section 6 is clamped fast between a sealing ring 18 on the annular end face of the nipple 10 and a screw collar 9 whose internal threads 19 matingly engage external threads 20 on the nipple 10. A cell section 5 of the housing 2 coaxially depends from the section 6 and houses an electrolytic cell. The next lower housing section 4 receives a water filter, and an electrically driven pump is arranged in the lowermost section 3 of the housing 2 from which the intake pipe 16 of the pump projects into a flexible hose 8 long enough to reach the bottom of the can 1.

Figure 2:
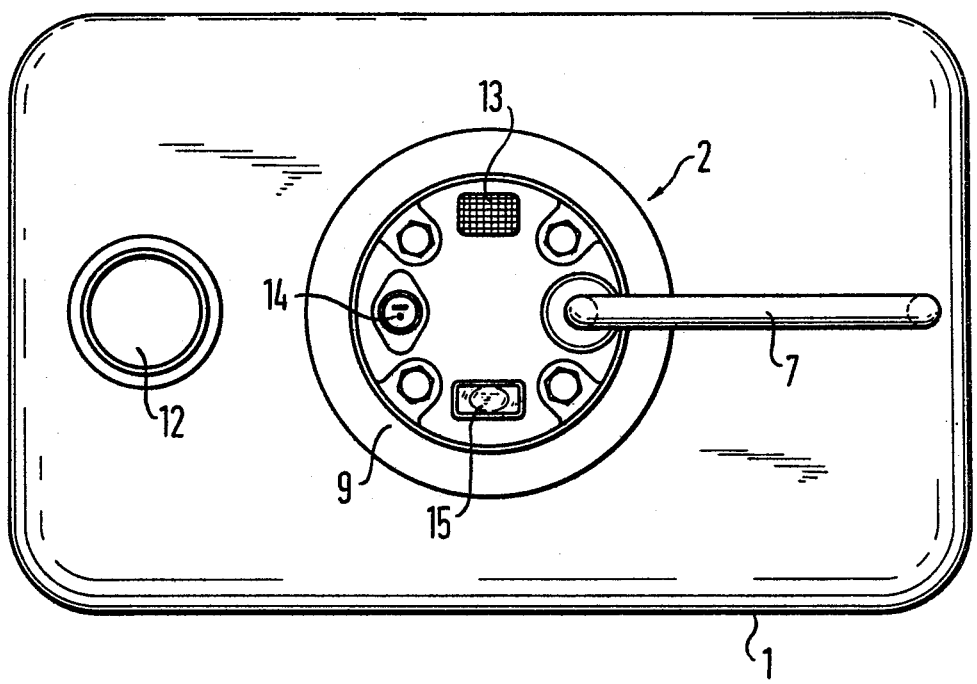
FIG. 2 is a top plan view of the apparatus of FIG. 1.

As is better seen in FIG. 2, the top wall of the housing 2 carries a light assembly 13, a plug 14 for connection to a source of electric current, and a push button starting switch 15. A discharge spout 7 is mounted in the top wall for pivoting movement about an upright axis.

The operating elements concealed in the housing 2 are closely similar to those of the modified purification unit illustrated in FIG. 3, and differ only in dimensions and spatial arrangement from those now to be described with reference to FIG. 3.

The housing 21 of the modified unit essentially consists of three plastic parts, generally of circular cross section about an upright axis. A cover plate 40 of the housing carries the light assembly 13, switch 15, and connector plug (not visible in FIG. 3). It is set into the top section 22 of a second plastic housing part having two additional sections 25, 33. The section 22 is secured in a nipple 10' of a water storage can 1', otherwise identical with the can 1, by a snap fit, a rib 11' of the housing section 22 being received in a groove of the nipple 10'. External threads 24 on the axially short section 25 of the second housing part connect the section to the third, generally cup-shaped housing part 23.

An integral partition 28 radially connects the section 25 to the reduced lowermost section 33 of the second housing part. The partition axially separates a control and power supply compartment 26, radially bounded by the housing section 22 from a cell 27 in the section 33. An integral pipe 48 extends upward from the partition 28 through the cover plate 49 and pivotally receives one end of the discharge spout 7. The section 33 and the housing part 23 define therebetween an annular chamber 34 which is upwardly sealed by the partition 28 and downwardly bounded by a radial plate 38. Radially elongated recesses in the top face of the plate 38 are axially aligned with the lower edge of the housing section 33 to provide connections between the cell 27 and the annular chamber 34. The bottom wall 43 of the housing part 23 and the plate 38 axially bound a pump chamber 44 which communicates with the chamber 34 through notches 47 in the circumference of the plate 38. A nipple 41 on the outer face of the bottom wall 43 is provided with a ball valve 42 spring biased toward the closed position and permitting fluid flow from the can 1' into the pump chamber 44 only. A tubular socket 39 integrally depending from the bottom wall 43 provides four feet for the purification unit, the feet being separated by openings 40. The hose 8, not shown in FIG. 3, normally depends from the nipple 41.

A rotary pump 46 is mounted in the chamber 44 to draw water into the chamber through the one-way valve 42. The pump is driven by an electric motor 29 in the control compartment 26, the output shaft 45 of the motor extending over almost the entire axial length of the housing part 23, but being only partly indicated. The pumped water is driven through the notches 47 into the annular chamber 34 and through a tubular filter 35 secured in circular grooves 36, 37 of the partition 28 and the plate 38. The filtrate enters the bottom of the cell 27 through the recesses in the plate 38 and rises between electrodes 30, 31, 32 in the cell, the electrodes 30, 31 being connected to a source of electrolyzing current by solid conductors, while the closely spaced bipolar electrodes 32 are mounted on insulators in a manner known and not specifically illustrated. Anodically purified water is discharged by the pump 46 from the cell 27 through the spout 7.

Figure 4:
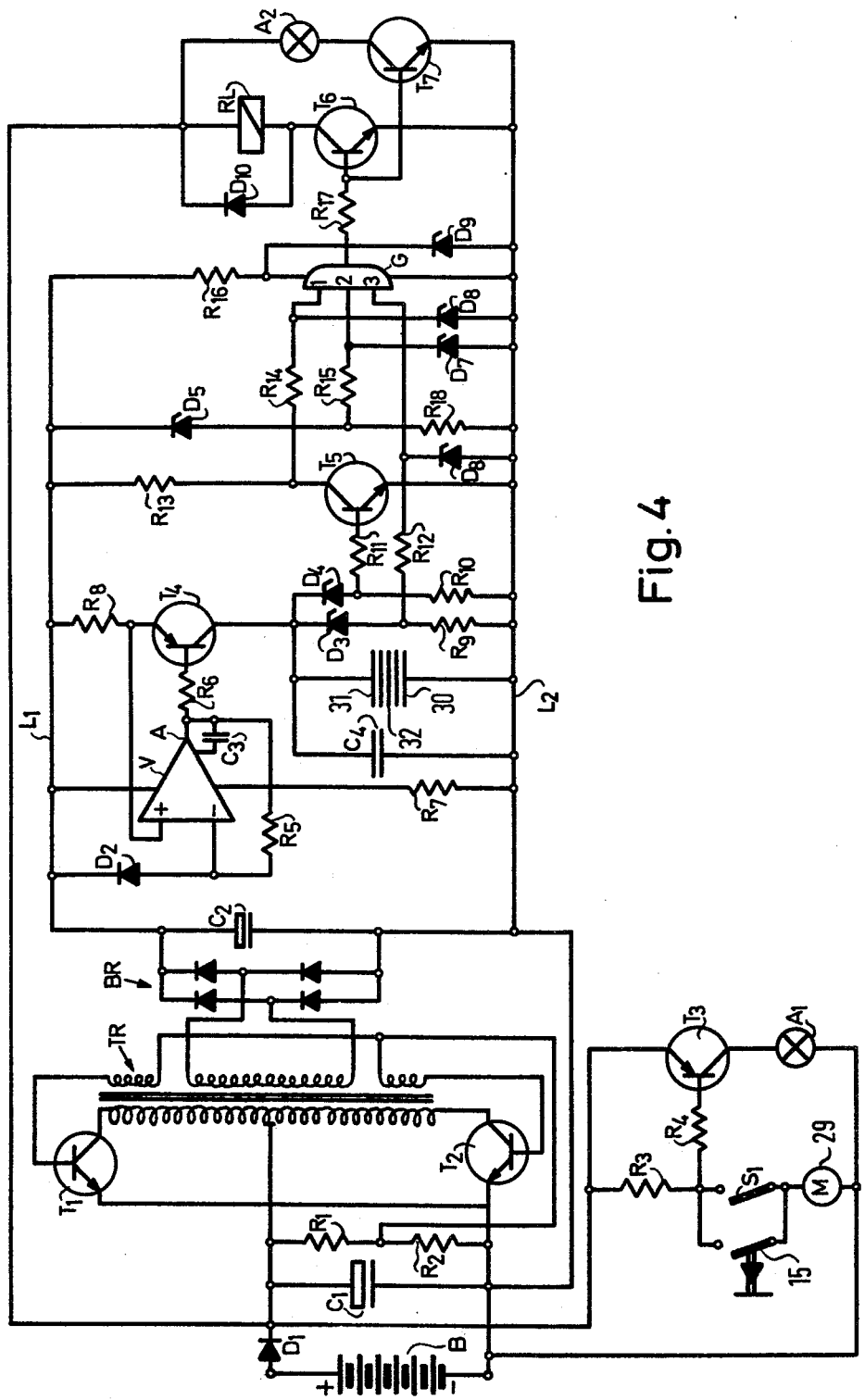
FIG. 4 diagrammatically illustrates electrical circuitry common to the devices of FIGS. 1 and 3.

FIG. 4 shows preferred circuitry for the power supply and controls of the water supply systems of the invention. It uses a 12-volt storage battery B as an external current source. The battery is connected through the connector 14 (not shown in FIG. 4) and a diode $D_1$ to the D.C. power supply circuit which includes two transistors $T_1$ and $T_2$ operated in push-pull. The emitters of the transistors $T_1$ and $T_2$ are connected in common to the tap of a voltage divider including resistors $R_1$ and $R_2$. The collectors of the transistors are connected to the end terminals of the primary winding of a transformer TR whose center tap is connected to the cathode of diode $D_1$. The secondary winding of transformer TR feeds a full-wave rectifier circuit BR. A capacitor $C_2$ is connected across the output of the rectifier circuit. A capacitor $C_1$ is connected in parallel with the battery B.

The oscillator constituted by the transistors $T_1$, $T_2$ and associated elements oscillates at a frequency determined by the self-capacitances of the circuit, the capacitance of the capacitor $C_1$ and the transformer inductances. The transformer TR operates as a step-up transformer.

A direct potential higher than the battery potential is derived from the capacitor $C_2$ for operation of the electrolytic cell and for the control circuits presently to be described. The potential is applied to the electrodes 30, 31 of the cell, and the bipolar electrodes 32 assume voltages according to their positions, the spacing between adjacent, oppositely charged electrode surfaces being not more than 4 mm, a spacing of only 1 mm being usually feasible and desirable.

The motor 29 driving the pump 46 is directly energized by the battery B. A fixed resistor $R_3$ and two parallel switches $S_1$, 15 control current flow to the motor 29. The afore-described starting switch 15 is manually operated by means of a push button. The switch $S_1$ is constituted by contacts of a relay RL which is operated by the control circuit in accordance with current flow through the electrolytic cell and with the potential applied across the cell, as will presently be described. A glow-type indicator lamp $A_1$ is connected from the negative terminal of the battery B to the collector of a transistor $T_3$ whose emitter is connected to the cathode of the diode $D_1$. The base of the transistor $T_3$ is connected to the junction of the switch $S_1$ and the resistor $R_3$ through a resistor $R_4$.

When the switch 15 or the switch $S_1$ is closed, current flows to the motor 29 through the resistor $R_3$. If the purification unit operates properly, the potential across the resistor $R_3$ is not sufficient to switch the transistor $T_3$ to the conductive state whereby the lamp $A_1$ remains dark. If the filter 35 is excessively clogged by impurities, the current through the motor 29 rises sufficiently to switch the transistor $T_3$ and thereby to energize the pilot lamp $A_1$ and to warn the user that the filter 35 needs to be replaced or cleaned.

The motor 29 and indicator $A_1$ are thus energized directly by the battery B while the electrolytic cell is energized by the output of the D.C. power supply described above. A current control circuit prevents excessive current drain from the battery B when water of unusually high conductivity is supplied to the cell. The current control circuit includes a fixed resistor $R_8$ in series with the collector - emitter circuit of a transistor $T_4$ and the electrodes 30, 31. To keep the current through the transistor $T_4$ substantially constant, the base of the transistor $T_4$ is connected through a resistor $R_6$ with the output A of a differential amplifier V whose direct input is connected to the emitter of the transistor $T_4$, and whose inverting input is connected to a source of reference potential. The resistor $R_6$ limits the base current of the transistor $T_4$. The source of reference potential is a Zener diode $D_2$ operated in inverse direction. The differential amplifier V compares the reference potential with the potential across the resistor $R_8$ and controls the transistor $T_4$ in such a manner that both potentials agree. A feedback resistor $R_5$ is arranged between the output A and the inverting input of the differential amplifier V and reduces the amplification of the amplifier V sufficiently to produce a linear response over the entire control range. A capacitor $C_3$, in connection with the feedback resistor $R_5$ provides frequency compensation. The amplifier V is energized through lines $L_1$, $L_2$ from the output of the D.C. power supply. Line $L_1$ will be referred to hereinbelow as the positive supply line, line $L_2$ as the ground line. A current feedback resistor $R_7$ is arranged between the current supply terminal of the differential amplifier V and the ground line $L_2$ and limits the base current of the transistor $T_4$ if the conductivity of the water between the electrodes 30, 31 is extremely low or if no water is present in the electrolytic cell. A capacitor $C_4$ arranged in parallel with the electrodes 30, 31 suppresses voltage spikes.

A safety circuit connected to the electrolytic cell stops the pump motor 29 and indicates the motor stoppage if conditions are not proper for safely purifying the water in the electrolytic cell. The motor is switched off by the contacts $S_1$ of the relay RL, and the deenergizing of the motor is indicated by a second pilot lamp $A_2$ in the light assembly 13. A diode $D_3$, arranged in the inverse direction, and a current limiting resistor $R_9$ are connected in one series circuit between the electrodes 30, 31, and a corresponding diode $D_4$ and a current limiting resistor $R_{10}$ in a second series circuit. As the conductivity of the water in the cell 27 increases, while the current through the cell is held constant by the afore-described current control circuit, the potential across the electrodes 30, 31 decreases and ultimately causes the diode $D_3$ to block a normally conductive path from the electrode 31 to input 3 of an AND gate G which is connected to the junction of the diode $D_3$ and the resistor 9 through a resistor $R_{12}$.

The output of the gate G is connected to the base of a transistor $T_6$ through a resistor $R_{17}$. The emitter-collector circuit of the transistor $T_6$ and the winding of the relay RL are connected in series across the poles of the battery B. The pilot lamp $A_2$ is similarly connected in series with a transistor $T_7$ across the battery poles. The base of the transistor $T_7$ is directly connected to the base of the transistor $T_6$. The relay RL and the pilot lamp $A_2$ are thus independent from any malfunction of the high-voltage supply, and the latter is not required to furnish operating current for the relay and the lamp $A_2$. The resistor $R_{17}$ which is interposed between the output terminal of the gate G and the bases of the transistors $T_6$, $T_7$ limits the base current. A diode $D_9$ and a resistor $R_{16}$ stabilize the voltage supplied to the gate G.

The pilot lamp $A_2$ lights up when conditions in the cell 27 are proper for operation. The transistors $T_6$ and $T_7$ deenergize the relay RL and the lamp $A_2$ if any one of the three input terminals of the gate does not receive a proper signal. The motor 29 is deenergized by the opening of switch $S_1$.

If the conductivity of the water in the cell 27 is too low, the voltage across the electrodes 30, 31 rises above the limit for which the purification unit is designed, and thus causes the diode $D_4$ to become conductive. Current flows through the resistor $R_{10}$ to ground line $L_2$. The base of a transistor $T_5$ is connected through a resistor $R_{11}$ with the junction of the diode $D_4$ and resistor $R_{10}$. The voltage at the base of transistor $T_5$ becomes more positive and the transistor $T_5$ is switched to the conductive state. The input 1 of the AND-gate G is connected to the collector of the transistor $T_5$ through a resistor $R_{14}$ and is switched off. A resistor $R_{13}$ limits the collector current of the conductive transistor $T_5$. Excessive voltage across the electrodes 30, 31 because of low water conductivity or for any other reason thus causes the pump 46 to stop and the light $A_2$ to be extinguished.

The input terminal 2 of the gate G is connected through a resistor $R_{15}$ to the junction of a diode $D_5$ and a resistor $R_{18}$ which are arranged in series circuit between the line $L_1$, $L_2$. If the voltage available at the capacitor $C_2$ decreases below the blocking voltage of the diode $D_5$, the input signal at input 2 blocks the AND gate G, the pump 46 stops and the pilot light $A_2$ is extinguished. Diodes $D_6$, $D_7$, $D_8$ are interposed respectively between the three input terminals of the gate G and the ground line $L_2$ to limit the potentials applied to the gate inputs. A diode $D_{10}$ is arranged parallel to the coil of the relay RL to protect the transistor $T_6$ against excessive potentials due to the self-inductance of the coil.

The control and power supply circuit illustrated in FIG. 4 permits the use of an automotive battery for operating the purification unit of the water supply system of the invention. Such a battery is often available where the water supply systems of the invention are of greatest utility. The output potential of such a battery is not always sufficient to operate an electrolytic cell for rapid and reliable anodic oxidation of impurities of the invention, and the power supply described above provides a voltage reserve adequate for purification of raw waters varying greatly in conducitivity. The power supply automatically controls cell voltage for the purification of aqueous liquids mainly consisting of rain water or containing some brackish water. Adequate operation with a range of water conductivity between 100 $\mu$S and 2000 $\mu$S (1 siemens = 1 mho) is ensured without intervention of the operator. Except under conditions of extreme microbial contamination and regardless of its conductivity, the water drawn from the can 1, 1' is free from viable, pathogenic microorganisms when discharged from the spout 7.

When equipped with the can 1, 1' the water supply system of the invention is self-contained to the extent of being independent of a local water source. However, the purification unit may be employed without the normally associated container. Thus, the intake pipe 16 or the nipple 41 may be connected to a water line or a remote water tank through a hose such as the hose 8, and purification units of the invention so equipped are well adapted to service in temporary dwellings, such as weekend houses, boats, or camping trailers equipped with a permanently installed water distribution system.

Figure 3:
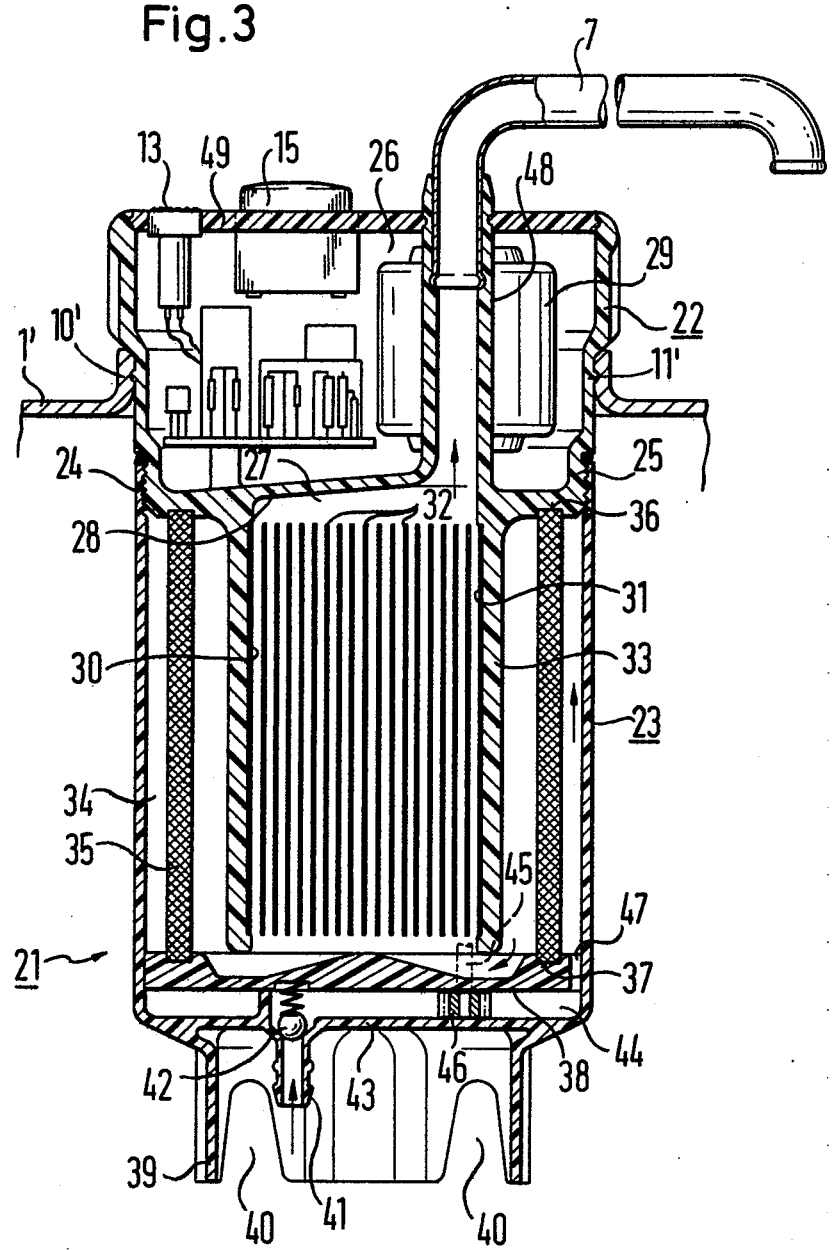
FIG. 3 illustrates apparatus of the invention closely similar to that of FIG. 1.

The purification units of the invention may be immersed partly in a natural body of water, and the unit illustrated in FIG. 3 is specifically equipped with the notched socket 39 as a stand for this purpose. When the purification unit is removed from the can 1', the can may be properly cleaned and disinfected, and then placed under the spout 7 to receive purified water for limited storage and for transportation elsewhere.

While a purification unit of the invention readily disinfects drinking water, ambient conditions may make it difficult to maintain a low microorganism count in the water after purification. If drinking water is to be stored, it is preferred to run the purification unit continuously on a body of previously treated water in the can 1, 1' and to return the water discharged from the spout 7 to the can through a hose connecting the spout with the nipple 12. Such repeated passage through the purification unit may also permit the production of safe drinking water from a raw water too badly contaminated to be disinfected by a single passage through the cell 27.

A storage battery is usually the only available source of electric current where the water supply system of the invention is most beneficial, but operation from alternating line voltage of 110 volts is possible by means of a conventional adapter without structural changes in the illustrated apparatus. Conversely, the power supply system shown in FIG. 4 is readily modified for operation on 110 volt AC, and may be provided with an adapter, internal or external, for operation on battery current.

Normal maintenance of the water supply system requires only the periodic cleaning or replacement of the filter element 35 after release of the housing part 23 from the threads 24 of the section 25 and withdrawal of the pump 46 with the plate 38 from the motor shaft 45 whose square end is slidably received in a mating opening of the pump impeller. While not explicitly illustrated, the filter element in the purification unit of FIG. 1 is axially juxtaposed to the electrolytic cell in the housing section 5, and its associated housing section 4 may similarly be released from the section 5 for access to the filter.

It should be understood, of course, that the foregoing disclosure relates only to preferred embodiments, and that it is intended to cover all changes and modifications of the examples of the invention herein chosen for the purpose of the disclosure which do not constitute departures from the spirit and scope of the invention set forth in the appended claims.

What is claimed is:

1. A water purification system comprising:

(a) an electrolytic cell adapted to hold a body of water to be purified;
(b) pump means including an electric motor for supplying said water to said cell and for discharging purified water from said cell;
(c) an electric battery;
(d) conductive means for directly connecting said battery to said motor and for thereby supplying electrical energy to said pump means; and
(e) direct-current power-supply circuit means connected to said battery and to said cell for receiving electrical energy from said battery and for furnishing to said cell a direct-current voltage exceeding the output voltage of said battery.

2. A system as set forth in claim 1, further comprising means defining a supply path for said water to be purified to said cell and a discharge path for said purified water, said electric motor drawing a current exceeding a predetermined value if one of said paths is clogged; and indicator means connected to said motor and responsive to said current for generating a malfunction signal when said current exceeds said value.

3. A system as set forth in claim 2, wherein said indicator means include a resistor connected in series with said motor, a switching transistor having an emitter-collector circuit and a base, an indicator connected in series with said emitter-collector circuit, and means conductively connecting said base to said resistor.

4. A system as set forth in claim 1, further comprising monitoring circuit means for monitoring the conductivity of said water to be purified and said direct-current voltage, for generating a stop signal when the value of at least one of the monitored quantities is ouside a predetermined operating range, and disconnecting means for disconnecting said motor from said battery in response to the generated signal.

5. A system as set forth in claim 4, wherein said monitoring circuit means include first monitoring means for monitoring said conductivity and furnishing a first signal when said conductivity is outside said predetermined operating range, second monitoring means for monitoring said direct-current voltage and furnishing a second signal when said direct-current voltage is outside of said predetermined operating range, logic circuit means connected to said first and second monitoring means for furnishing said stop signal in response to said first and second signals, a relay including a coil and a pair of contacts, switching means for changing current flow through said coil in response to said stop signal, said disconnecting means including said pair of contacts and means connecting said contacts in series with said battery and said motor, said coil opening said contacts in response to said changing of current flow.

6. A system as set forth in claim 5, wherein said switch means include a transistor having an emitter-collector circuit connected in series with said coil and a base connected to said logic circuit means for receiving said stop signal.

7. A system as set forth in claim 6, further comprising means for directly connecting the series circuit constituted by the emitter-collector circuit of said transistor and by said coil to said battery.

8. A system as set forth in claim 7, further comprising indicator means connected to said battery for furnishing an indication when said motor is disconnected from said battery.

9. A system as set forth in claim 5, further comprising a manually operable starting switch having contacts connected in parallel with said pair of contacts.

10. A system as set forth in claim 5, further comprising current control means connected to said cell and to said power-supply circuit means for maintaining a constant current through said cell, said first monitoring means including voltage monitoring means for monitoring the voltage across said cell.

11. A system as set forth in claim 10, wherein said voltage monitoring means include a first diode-resistor circuit connected in parallel with said cell, said second monitoring means include a second diode-resistor circuit connected to said power-supply circuit means for receiving said direct current voltage, and said logic circuit means include an AND gate having first and second inputs connected to said first and second diode-resistor circuits respectively.

12. A system as set forth in claim 1, wherein said direct-current power supply circuit means include a step-up transformer having primary and secondary windings, an oscillator circuit connected to said primary winding, a full-wave rectifier circuit connected to said secondary winding, and a capacitor connected across said full-wave rectifier circuit.

* * * * *